US008629264B2

(12) United States Patent
Reed et al.

(10) Patent No.: US 8,629,264 B2
(45) Date of Patent: Jan. 14, 2014

(54) GRAVITY FLOW FLUIDIC DEVICE FOR NUCLEIC ACID EXTRACTION

(75) Inventors: Michael W. Reed, Lake Forest Park, WA (US); Daniel P. Gestwick, Seattle, WA (US)

(73) Assignee: Blood Cell Storage, Inc., Seattle, WA (US)

( * ) Notice: Subject to any disclaimer, the term of this patent is extended or adjusted under 35 U.S.C. 154(b) by 0 days.

(21) Appl. No.: 13/475,702

(22) Filed: May 18, 2012

(65) Prior Publication Data

US 2012/0296075 A1  Nov. 22, 2012

Related U.S. Application Data

(60) Provisional application No. 61/488,124, filed on May 19, 2011.

(51) Int. Cl.
*C07H 1/08* (2006.01)

(52) U.S. Cl.
USPC ....................................................... 536/25.41

(58) Field of Classification Search
USPC ....................................................... 536/25.41
See application file for complete search history.

(56) References Cited

U.S. PATENT DOCUMENTS

| | | | |
|---|---|---|---|
| 4,883,867 | A | 11/1989 | Lee |
| 5,155,018 | A | 10/1992 | Gillespie |
| 5,234,809 | A | 8/1993 | Boom |
| 5,405,519 | A | 4/1995 | Schwartz |
| 5,587,128 | A | 12/1996 | Wilding |
| 5,599,664 | A | 2/1997 | Schwartz |
| 5,658,548 | A | 8/1997 | Padhye |
| 5,720,928 | A | 2/1998 | Schwartz |
| 5,808,041 | A | 9/1998 | Padhye |
| 5,989,431 | A | 11/1999 | Evans |
| 5,994,056 | A | 11/1999 | Higuchi |
| 6,147,198 | A | 11/2000 | Schwartz |
| 6,150,089 | A | 11/2000 | Schwartz |
| 6,168,948 | B1 | 1/2001 | Anderson |
| 6,171,785 | B1 | 1/2001 | Higuchi |
| 6,174,671 | B1 | 1/2001 | Anantharaman |
| 6,194,562 | B1 | 2/2001 | Smith |
| 6,218,531 | B1 | 4/2001 | Ekenberg |
| 6,294,136 | B1 | 9/2001 | Schwartz |
| 6,340,567 | B1 | 1/2002 | Schwartz |
| 6,377,721 | B1 | 4/2002 | Walt |
| 6,383,393 | B1 | 5/2002 | Colpan |
| 6,448,012 | B1 | 9/2002 | Schwartz |
| 6,489,112 | B1 | 12/2002 | Hadd |
| 6,509,158 | B1 | 1/2003 | Schwartz |
| 6,610,256 | B2 | 8/2003 | Schwartz |
| 6,617,105 | B1 | 9/2003 | Rudi |
| 6,649,378 | B1 | 11/2003 | Kozwich |
| 6,713,263 | B2 | 3/2004 | Schwartz |
| 6,720,417 | B1 | 4/2004 | Walter |
| 6,814,934 | B1 | 11/2004 | Higuchi |
| 6,821,757 | B2 | 11/2004 | Sauer |
| 7,173,124 | B2 | 2/2007 | Deggerdal |
| 7,238,530 | B2 | 7/2007 | Goudsmit |
| 7,385,043 | B1 | 6/2008 | Kramer |
| 7,416,892 | B2 | 8/2008 | Battrell |
| 8,163,535 | B2 | 4/2012 | Reed |
| 2001/0026921 | A1 | 10/2001 | Rabbani |
| 2002/0006623 | A1 | 1/2002 | Bradley |
| 2002/0025529 | A1 | 2/2002 | Quake |
| 2002/0155586 | A1 | 10/2002 | Cheng |
| 2002/0157119 | A1 | 10/2002 | Beachy |
| 2002/0164816 | A1 | 11/2002 | Quake |
| 2003/0138941 | A1 | 7/2003 | Gong |
| 2004/0014070 | A1 | 1/2004 | Pinsl-Ober |
| 2004/0086930 | A1 | 5/2004 | Tereba |
| 2004/0122222 | A1 | 6/2004 | Sakurai |
| 2004/0152085 | A1 | 8/2004 | Terlesky |
| 2004/0215011 | A1 | 10/2004 | Deggerdal |
| 2004/0241721 | A1* | 12/2004 | Gjerde et al. ............... 435/6 |
| 2005/0142565 | A1 | 6/2005 | Samper |
| 2005/0191760 | A1 | 9/2005 | Heath |
| 2005/0211559 | A1 | 9/2005 | Kayyem |
| 2005/0214765 | A1 | 9/2005 | Reitan |
| 2006/0029972 | A1 | 2/2006 | Lorenz |
| 2006/0166223 | A1 | 7/2006 | Reed |

(Continued)

FOREIGN PATENT DOCUMENTS

| | | |
|---|---|---|
| EP | 0 430 248 A2 | 6/1991 |
| EP | 1 237 832 B1 | 8/2002 |

(Continued)

OTHER PUBLICATIONS

Bhattacharyya, A., and C.M. Klapperich, "Thermoplastic Microfluidic Device for On-Chip Purification of Nucleic Acids for Disposable Diagnostics," Analytical Chemistry 78(3):788-792, Feb. 2006.

Boom, R., et al., "Rapid and Simple Method for Purification of Nucleic Acids," Journal of Clinical Microbiology 28(3):495-503, Mar. 1990.

Breadmore, M.C., et al., "Microchip-Based Purification of DNA From Biological Samples," Analytical Chemistry 75(8):1880-1886, Apr. 2003.

Cady, N.C., et al., "Nucleic Acid Purification Using Microfabricated Silicon Structures," Biosensors & Bioelectronics 19(1):59-66, Oct. 2003.

"DNA Quantitation Kit, Fluorescence Assay," Product Code: DNA-QF, 2000-2001 Product Catalog: Molecular Biology, Sigma-Aldrich, St. Louis, Mo., at least as early as Jun. 2000, p. 109.

(Continued)

*Primary Examiner* — Wu-Cheng Winston Shen
*Assistant Examiner* — Yih-Horng Shiao
(74) *Attorney, Agent, or Firm* — Christensen O'Connor Johnson Kindness PLLC (57) ABSTRACT

A system, method, and kit for extracting nucleic acid from a sample containing nucleic acid uses an extraction device with an elongate channel. Fluids are provided to the channel via gravity feed to the inlet port. The flow rate and other flow behavior may be controlled with a siphon provided at the outlet port.

27 Claims, 5 Drawing Sheets

(56) References Cited

U.S. PATENT DOCUMENTS

| | | | |
|---|---|---|---|
| 2006/0188973 A1 | 8/2006 | Xu | |
| 2006/0216239 A1 | 9/2006 | Zhang | |
| 2009/0215125 A1* | 8/2009 | Reed et al. | 435/91.2 |
| 2010/0028980 A1 | 2/2010 | Hasson | |
| 2011/0203688 A1 | 8/2011 | Reed | |

FOREIGN PATENT DOCUMENTS

| | | |
|---|---|---|
| EP | 1 388 588 A1 | 2/2004 |
| EP | 1 529 841 B1 | 5/2005 |
| EP | 1 607 748 A1 | 12/2005 |
| EP | 1 655 366 A2 | 5/2006 |
| KR | 10-1005924 B1 | 1/2010 |
| WO | 99/09042 A2 | 2/1999 |
| WO | 00/40697 A1 | 7/2000 |
| WO | 02/22265 A1 | 3/2002 |
| WO | 2004/040001 A2 | 5/2004 |
| WO | 2004/061085 A2 | 7/2004 |
| WO | 2004/071662 A1 | 8/2004 |
| WO | 2005/007895 A1 | 1/2005 |
| WO | 2005/066343 A1 | 7/2005 |
| WO | 2005/073691 A1 | 8/2005 |

OTHER PUBLICATIONS

"DNA Quantitation Kit, Fluorescence Assay," Product Information / Technical Bulletin, Catalog No. DNAQF, Sigma-Aldrich, St. Louis, Mo., at least as early as 2001, 4 pages.

Duncan, R.E., and P.T. Gilham, "Isolation of Transfer RNA Isoacceptors by Chromatography on Dihydroxyboryl-Substituted Cellulose, Polyacrylamide, and Glass," Analytical Biochemistry 66(2):532-539, Jun. 1975.

Gao, J., and M.B. Chan-Park, "Adhesive Behavior of DNA Molecules on Silicon Wafers Treated by Argon and Oxygen Plasma," Surface and Coatings Technology 194(2-3):244-250, May 2005.

Gobbers, E., et al., "Efficient Extraction of Virus DNA by NucliSens Extractor Allows Sensitive Detection of Hepatitis B Virus by PCR," Journal of Clinical Microbiology 39(12):4339-4343, Dec. 2001.

Kim, J.-H., et al., "A Disposable DNA Sample Preparation Microfluidic Chip for Nucleic Acid Probe Assay," Proceedings of the 15th IEEE International Conference on Micro Electro Mechanical Systems, Las Vegas, Jan. 20-24, 2002, pp. 133-136.

Lee, C.-Y., Jr., et al., "Integrated Microfluidic Systems for DNA Analysis," Proceedings of the IEEE International Conference on Robotics and Biomimetics, Shenyang, China, Aug. 22-26, 2004, pp. 284-289.

Legendre, L.A., et al., "A Simple, Valveless Microfluidic Sample Preparation Device for Extraction and Amplification of DNA From Nanoliter-Volume Samples," Analytical Chemistry 78(5):1444-1451, Mar. 2006.

Liu, W.-T., and L. Zhu, "Environmental Microbiology-on-a-Chip and Its Future Impacts," Trends in Biotechnology 23(4):174-179, Apr. 2005.

Malic, L., et al., "Current State of Intellectual Property in Microfluidic Nucleic Acid Analysis," Recent Patents on Engineering 1(1):71-88, Feb. 2007.

McCaustland, K.A., et al., "Application of Two RNA Extraction Methods Prior to Amplification of Hepatitis E Virus Nucleic Acid by the Polymerase Chain Reaction," Journal of Virological Methods 35(3):331-342, Dec. 1991.

Münchow, G., et al., "Automated Chip-Based Device for Simple and Fast Nucleic Acid Amplification," Expert Review of Molecular Diagnostics 5(4):613-620, Jul. 2005.

Nakagawa, T., et al., "Fabrication of Amino Silane-Coated Microchip for DNA Extraction From Whole Blood," Journal of Biotechnology 116(2):105-111, Mar. 2005.

Nanassy, O.Z., et al., "Capture of Genomic DNA on Glass Microscope Slides," Analytical Biochemistry 365(2):240-245, Jun. 2007.

Reed, M.W., and O.Z. Nanassy, "Device and Method for Extraction and Analysis of Nucleic Acids from Biological Samples," U.S. Appl. No. 13/435,440, filed Mar. 30, 2012.

Rohland, N., and M. Hofreiter, "Comparison and Optimization of Ancient DNA Extraction," Biotechniques 42(3):343-352, Mar. 2007.

Steiner, J.J., et al., "A Rapid One-Tube Genomic DNA Extraction Process for PCR and RAPD Analyses," Nucleic Acids Research 23(13)2569-2570, Jul. 1995.

Thompson, J.D., et al., "Extraction of Cellular DNA From Crude Cell Lysate With Glass," Nucleic Acids Research 18(4):1074, Feb. 1990.

Tian, H., et al., "Evaluation of Silica Resins for Direct and Efficient Extraction of DNA From Complex Biological Matrices in a Miniaturized Format," Analytical Biochemistry 283(2):175-191, Aug. 2000.

Vogelstein, B., and D. Gillespie, "Preparative and Analytical Purification of DNA From Agarose," PNAS (Proceedings of the National Academy of Sciences USA) 76(2):615-619, Feb. 1979.

Waters, L.C., et al., "Microchip Device for Cell Lysis, Multiplex PCR Amplification, and Electrophoretic Sizing," Analytical Chemistry 70(1):158-162, Jan. 1998.

Weigl, B.H , et al., "Lab-on-a-Chip for Drug Development," Advanced Drug Delivery Reviews 55(3):349-377, Feb. 2003.

Wolfe, K.A., "Toward a Microchip-Based Solid-Phase Extraction Method for Isolation of Nucleic Acids," Electrophoresis 23(5):727-733, Mar. 2002.

Zhong, R., et al., "Fabrication of Two-Weir Structure-Based Packed Columns for On-Chip Solid-Phase Extraction of DNA," Electrophoresis 28(16):2920-2926, Aug. 2007.

"QIAamp © DNA Blood Mini/Maxi Handbook," 3d ed., Apr. 2010, © 2000-2010 QIAGEN, <http://www.qiagen.com>.

International Search Report and Written Opinion mailed Dec. 27, 2012, issued in corresponding International Application No. PCT/US2012/038658, filed May 18, 2012, 7 pages.

* cited by examiner

GRAVITY FLOW FLUIDIC DEVICE FOR NUCLEIC ACID EXTRACTION

CROSS-REFERENCE TO RELATED APPLICATION

This application claims the benefit of U.S. Provisional Application No. 61/488,124, filed May 19, 2011, which is incorporated herein by reference.

BACKGROUND

Rapid analysis of nucleic acids from biological samples has been advanced by the development of microfluidic technologies capable of extracting nucleic acids from cell lysates and other sources. Rapid extraction methodologies can be combined with amplification techniques such as polymerase chain reaction (PCR) to provide useful quantities of nucleic acids from minute samples of blood, tissue, cultured cells, or other biological materials. These microfluidic technologies have been widely adopted in biomedical research laboratories, permitting, for example, high-throughput screening of cloned DNA "libraries" from cultured bacteria or other host cells.

The need for devices, systems, and methods for extracting nucleic acids from biological samples is well-recognized, and particular devices and methods are known in the art. Commonly used methods for extracting DNA on such a small scale exploit the tendency for DNA to bind to materials such as silica gel, silica membranes, porous glass, or diatomaceous earth. One such system provides a microcentrifuge tube containing the DNA binding media (known as a "spin column"). The sample is loaded into the tube and spun in a centrifuge, whereby the DNA is captured and the liquid phase containing contaminants passes through to the bottom of the tube. Such a procedure is disclosed in, for example, U.S. Pat. No. 6,821,757, to Sauer et al. Although spin column technology has been widely adopted by the research community, the resulting DNA is often of low quality for use in downstream applications such as PCR, and the need to pipette multiple samples into open tubes results in a significant risk of sample contamination. Moreover, such methods are time-consuming when performed manually and very expensive to automate.

One or more of the present inventors have disclosed particular methods and systems for extracting nucleic acids in U.S. Pat. No. 8,163,535, to Reed et al., which is hereby incorporated by reference in its entirety; and in U.S. patent application Ser. No. 12/948,566, to Reed et al., published as US 2011/0203688 A1 on Aug. 25, 2011, which is also hereby incorporated by reference in its entirety. These methods and systems employ a smooth glass surface for capturing nucleic acids and provide certain advantages over spin columns, including simplified work flow and resistance to contamination.

The successful use of rapid DNA extraction techniques in research has led to an interest in developing devices and processes through which this technology can be used in medical applications such as point-of-care diagnosis or testing of blood components. Recent progress toward more simple and compact devices has been reviewed by Malic et al., *Recent Patents on Engineering* 1:71-88, 2007. Despite these recent advances, there remains a need in the art for devices and processes by which high-quality DNA and RNA can be rapidly and economically extracted from samples containing nucleic acids.

SUMMARY OF THE INVENTION

Within one aspect of the invention there is provided a process for extracting nucleic acid from a solution. The process comprises the steps of (a) providing a conduit comprising a binding channel having an inner surface, a first port, and a second port, wherein the first port and the second port are in fluid communication with the binding channel; (b) introducing a solution containing nucleic acid into the binding channel such that the solution is in contact with the inner surface and at least a portion of the nucleic acid binds to the inner surface to produce bound nucleic acids and a residual solution; (c) positioning a siphon tube having a first end connected to the second port such that a second end of the siphon tube is open to ambient pressure, a portion of the siphon tube is disposed at an elevation above the channel and the second end is not above the first end; and (d) fluidly connecting a reservoir of first wash buffer disposed at an elevation above the binding channel to the first port such that gravity forces the first wash buffer to flow through the first port into the binding channel, the first wash buffer thereby displacing the residual solution from the binding channel and through the siphon tube, whereby the bound nucleic acid is washed. Within one embodiment, the process further comprises introducing a gas bubble into the binding channel between the nucleic acid solution and the wash buffer. With a related embodiment the gas bubble is air. Within another related embodiment, the reservoir of first wash buffer is connected to the first port through an elongate tube that is initially filled with air, and the gas bubble is introduced into the binding channel by the first wash buffer displacing air from the elongate tube into the binding channel. Within another embodiment, the process further comprises waiting for the reservoir of first wash buffer to flow into the binding channel, and then fluidly connecting a reservoir of second wash buffer disposed at an elevation above the binding channel to the first port such that gravity forces the second wash buffer to flow through the binding channel displacing the first wash buffer, whereby the first wash buffer flows through the siphon tube. Within a further embodiment, the second end of the siphon tube is disposed within a vented outflow receptacle. Within an additional embodiment, the second end of the siphon tube is disposed at an elevation lower than the first end of the siphon tube. Within a further embodiment, a flow rate of the first wash buffer through the binding channel is controlled by setting the elevation of the second end of the siphon tube. Within another embodiment, the binding channel comprises a lumen formed by a smooth glass tube. Within a related embodiment, the lumen has a transverse cross section shape that is one of circular, oval, and elliptical. In another related embodiment, the lumen is a linear lumen with a longitudinal axis and is optionally tapered along the longitudinal axis. Within a different embodiment, the lumen is serpentine. Within another embodiment, the binding channel comprises a flow path cooperatively defined by a plurality of stacked, planar lamina. Within a further embodiment, the channel is serpentine. Within another embodiment, the conduit further comprises an inlet channel providing a fluid connection between the first port and the binding channel and an outlet channel providing a fluid connection between the second port and the binding channel. Within an additional embodiment, the process further comprises removing the first wash buffer from the binding channel by flowing gas from a source of pressurized gas through the binding channel. Within another embodiment, the process further comprises drying the bound and washed nucleic acid by flowing gas from a source of pressurized gas through the binding channel. Within a further embodiment, the solution containing nucleic acid comprises a lysate solution including ethanol. Within another embodiment, the process further comprises eluting the bound nucleic acid from the inner surface, for example eluting with a buffer that exhibits a change in fluorescence intensity in the presence of nucleic acid. Within other embodiments, the inner surface of the binding channel is essentially free of nucleic acid-specific binding sites, or the inner surface of the binding channel comprises nucleic acid-specific binding sites. Within another embodiment, the inner surface of the binding channel comprises a glass surface. Within a related embodiment, the glass surface is an unmodified, smooth glass surface. Within another embodiment, the binding channel has at least one dimension that is less than 1.0 mm. Within a further embodiment, the reservoir of first wash buffer has a reservoir volume that is sufficient to fill the binding channel before the fluid in the reservoir of first wash buffer drops below a highest level in the siphon. Within an additional embodiment, one of the first and second inlet ports is configured to sealingly receive a pipette tip.

Within a second aspect of the invention there is provided a kit for extracting nucleic acid from a sample. The kit comprises (a) a device defining an elongate channel having an inner surface that is suitable for capturing nucleic acids in a solution, the device further comprising a first port fluidly connected to the elongate channel, and a second port fluidly connected to the elongate channel; (b) a reservoir comprising a barrel with a body portion defining a first volume and a tip portion defining a through lumen fluidly connected to the first volume, wherein the tip portion is configured to fluidly engage the first port; and (c) a tubular siphon configured to fluidly engage the second port and to be positioned to siphon a liquid from the elongate binding channel. Within one embodiment, the reservoir barrel contains a wash buffer solution. Within another embodiment, the reservoir barrel contains a lysing agent. Within a related embodiment, the lysing agent comprises a protease. Within another embodiment, the reservoir barrel further contains a mixing ball. Within an additional embodiment, the kit further comprises a second reservoir containing a second wash buffer solution different from the first wash buffer solution, the second reservoir having a tip portion defining a lumen and configured to fluidly engage the second port. Within a related embodiment, the tip first portions of the first and second reservoirs further comprise a Luer-type fitting. Within another embodiment, the kit further comprises a vented outflow receptacle having an aperture sized to receive the siphon. Within a further embodiment, the kit further comprises a sealed package containing a binding buffer. Within a related embodiment, the sealed package includes two compartments separated by a frangible seal. Within a further related embodiment, one of the two compartments contains a chaotropic salt solution, and the other of the two compartments contains ethanol. Within another related embodiment, the chaotropic salt solution comprises one of guanidinium thiocyanate, guanidine hydrochloride, sodium iodide, and sodium perchlorate. Within an additional embodiment, the reservoir further comprises a plunger that slidably engages the barrel body portion and a venting aperture disposed at an intermediate location such that the aperture vents the barrel when the plunger is disposed above the venting aperture.

These and other aspects of the invention will become evident upon reference to the following detailed description of the invention and the accompanying drawings.

All references disclosed herein are incorporated by reference in their entirety.

Disclosed numerical ranges include their endpoints.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The present invention is directed to methods, systems, and kits for the extraction of nucleic acids, including deoxyribonucleic acids (DNA) and ribonucleic acids (RNA), from samples containing nucleic acids, for example lysates. As used herein, the term "biological sample" means a sample containing cells or cell components and includes any sample, liquid or solid, that contains nucleic acids. Suitable biological samples that can be used within the invention include, without limitation, cell cultures, culture broths, cell suspensions, tissue samples, cell lysates, cleared cell lysates, whole blood, serum, buffy coat, urine, feces, cerebrospinal fluid, semen, saliva, wound exudate, viruses, mitochondria, and chloroplasts. In one embodiment, the sample is blood or a blood product (e.g., platelets), and the nucleic acids that are extracted are those from contaminant bacterial pathogens in the blood or blood product. In another example, a swab, such as a nasal swab, is used to obtain a biological sample. The swab can be combined with a universal transport medium for stabilization during storage and transportation. To extract nucleic acids, samples are combined with a binding buffer, for example a buffer having salt (e.g., KCl) at a concentration of at least 0.5 M to about 2 M or more depending on solubility, or a chaotrope (e.g., guanidine HCl or guanidine thiocyanate) at a concentration of at least 1 M to about 6 M or the limit of solubility. Binding of nucleic acids is ordinarily done at a pH of approximately 5 to 8, preferably about 6.

DNA obtained or extracted using the present invention has been found to be of high quality for downstream applications, including amplification and the like.

Within the present invention, nucleic acids are captured by binding to an inner surface of a binding channel. Materials that bind nucleic acids are known in the art, and include surfaces that are modified by attachment of specific binding agents as well as surfaces that bind nucleic acids non-specifically. An example of the latter type of surface is smooth glass, as disclosed by, for example, U.S. Pat. No. 8,163,535, to Reed et al. In comparison to porous glass and modified glass surfaces (e.g., glass surfaces with scored, etched, or micro-engineered surfaces to enhance the surface area), smooth extraction surfaces are easy to wash free of enzymes, metals (e.g., heme), and other protein contaminants that can interfere with PCR-based assays. PCR yields are thereby improved and variability decreased.

As used herein, an "unmodified smooth glass surface" means a glass surface having a smoothness corresponding to that of a standard microscope slide, Pasteur pipette, glass capillary, or the like, wherein the surface has not been etched or otherwise altered to increase its surface area, and wherein it has not been modified to specifically bind nucleic acids as disclosed below. Specifically excluded from "smooth glass" is porous glass that is known in the art to capture nucleic acids, commonly in bead, frit, or membrane form. Suitable smooth glass materials for use within the present invention include but are not limited to soda lime glass, borosilicate glass, zinc titania glass, and silica glass. In certain embodiments of the present invention, the extraction surface is formed with glass tubing, which is readily available in a variety of sizes, for example, glass capillaries, chromatography columns, condenser tubes, syringes, rods, and the like having smooth glass surfaces. Nucleic acid-specific binding sites may be provided by modifying a surface with moieties known to specifically bind nucleic acids (or a desired subset of nucleic acids), such as surface charges or binding sites provided by immobilized oligonucleotides, minor groove binding agents, intercalating agents, or the like. A binding channel or surface that is "essentially free of nucleic acid-specific binding sites" is one that does not contain an amount of such sites sufficient to give a statistically significant increase in nucleic acid binding as compared to glass.

Devices of the present invention allow the extracted nucleic acids to be concentrated. For example, DNA captured from a 0.5-mL sample can be concentrated in 0.1 mL of elution buffer by sweeping the buffer through the device. This concentration effect is valuable for dilute samples or pathogen detection with improved sensitivity.

In contrast to the spin columns that are currently in widespread use, the present invention incorporates a nucleic acid extraction device that can be closed off from the outside environment. The invention thus provides systems in which the contents of the extraction device are essentially isolated from the environment, although these systems comprise provisions that allow for introduction of samples and reagents, and removal of waste products, washes, and extracted nucleic acids. For many applications, such closed systems are preferred because they are inherently resistant to contamination.

Devices of the present invention are designed for ease of use and also for ease of construction and assembly. In exemplary embodiments, movement of fluids through the devices does not require external power sources, power supplies, or active valving. In addition, the devices are designed to have improved resistance to contamination, in comparison with standard spin columns. The flow-through design of the extraction devices is flexible with regard to sample and reagent volumes, allowing dilute nucleic acid samples to be concentrated in the extraction process, and further allows quick drying of the internal channels using filtered air circulation. The transparent walls of exemplary embodiments of the binding channels permit quantification of nucleic acids within the device, such as through the use of a fluorometer. Multiple washing and drying steps can be automated, eliminating the need for manual manipulation of the device after sample loading and allowing more controlled timing of steps.

Figure 1A:
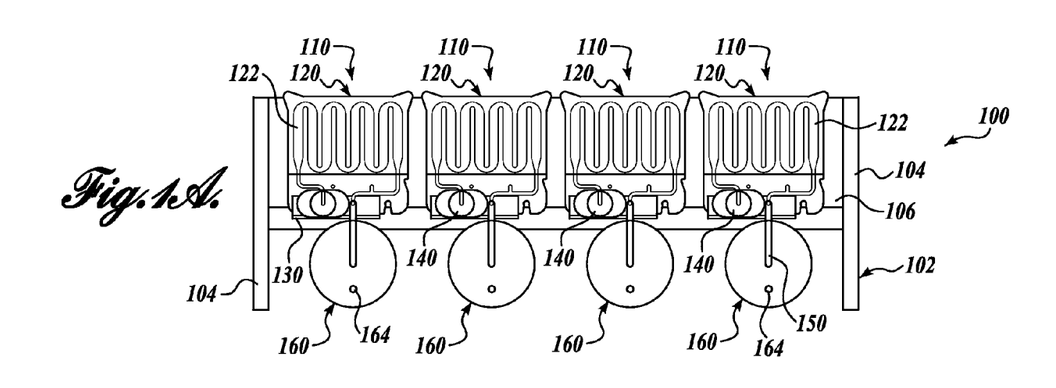
FIG. 1A is a plan view of a nucleic acid extraction system in accordance with the present invention.
Figure 1B:
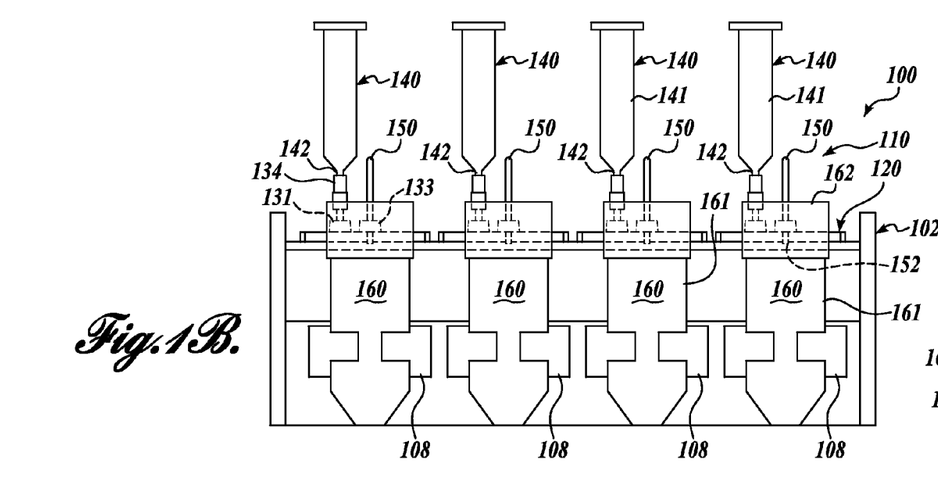
FIG. 1B is a front view of the nucleic acid extraction system shown in FIG. 1A.
Figure 1C:
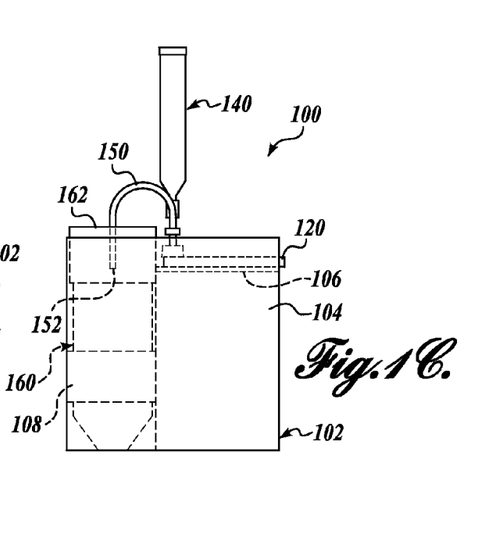
FIG. 1C is a right side view of the nucleic acid extraction system shown in FIG. 1A.

FIGS. 1A, 1B, and 1C show a plan view, front view, and side view, respectively, of an exemplary gravity feed nucleic acid extraction system 100, in accordance with the present invention. This embodiment comprises four substantially identical extraction subsystems 110. It will be apparent that more or fewer extraction subsystems 110 may be used. It is also contemplated by the present invention that the individual subsystems 110 may not all be identical. For example, each extraction subsystem 110 may be optimized for different types of biological samples. Alternatively, the extraction subsystems 110 may differ (e.g., having differing extraction channel length or cross sectional area), to increase the effectiveness and sensitivity of the system 100 for use with a diversity of nucleic acid-containing fluids.

Figure 2:
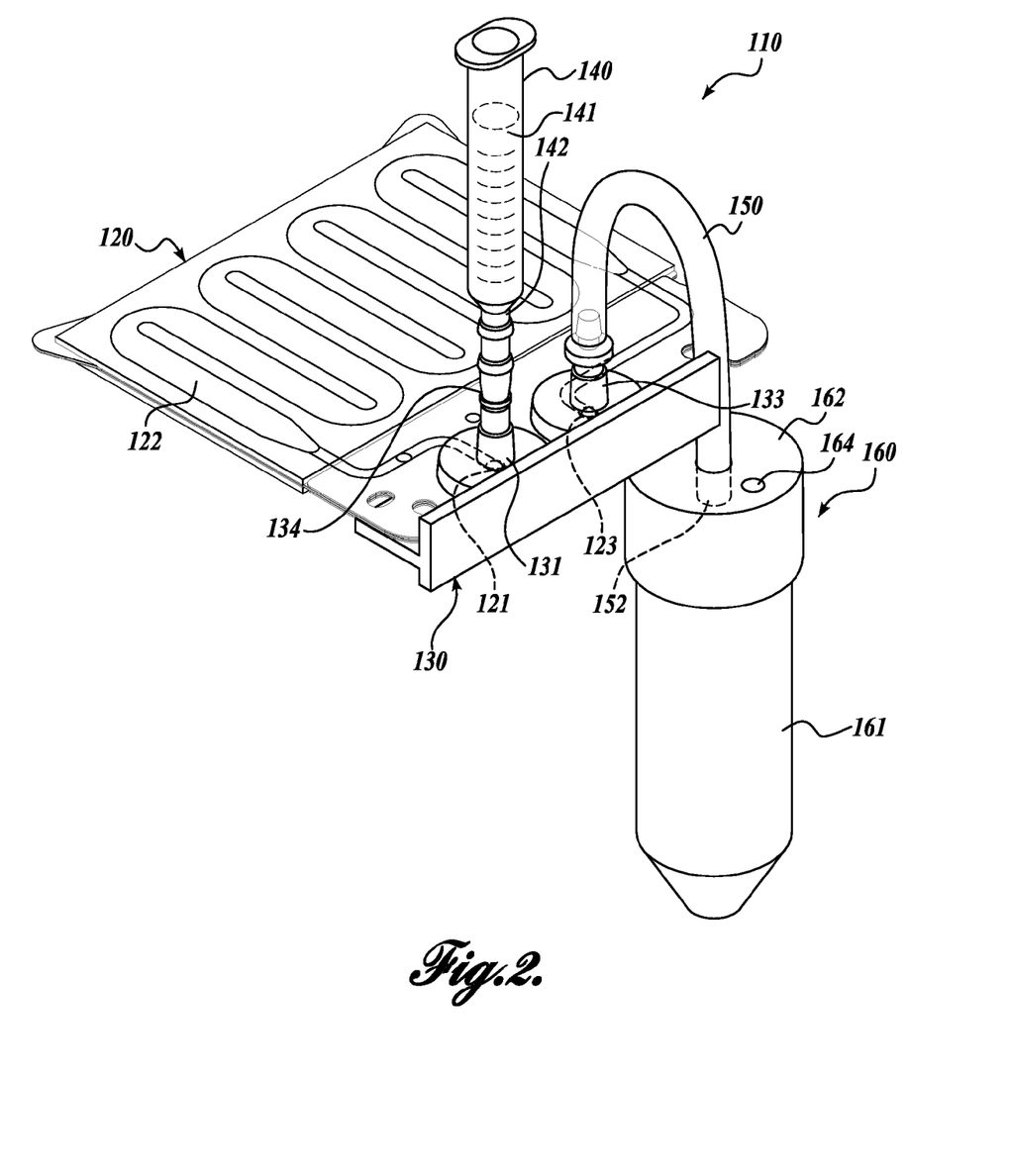
FIG. 2 is a perspective view of an extraction subsystem for the system shown in FIG. 1A.

In this exemplary embodiment the system 100 includes a support apparatus or bench 102 comprising upright members 104 that support a support surface 106. Each extraction subsystem 110 includes a nucleic acid extraction device 120 that is supported on the bench 102. FIG. 2 shows a single extraction subsystem 110, in isolation.

Support apparatus 102 is shown for illustrative purposes and is not intended to be limiting. While it is convenient to retain the components of system 100 in such a support, those skilled in the art will recognize that there is wide latitude in the design of this element, up to and including holding the components in the user's hand.

Figure 3:
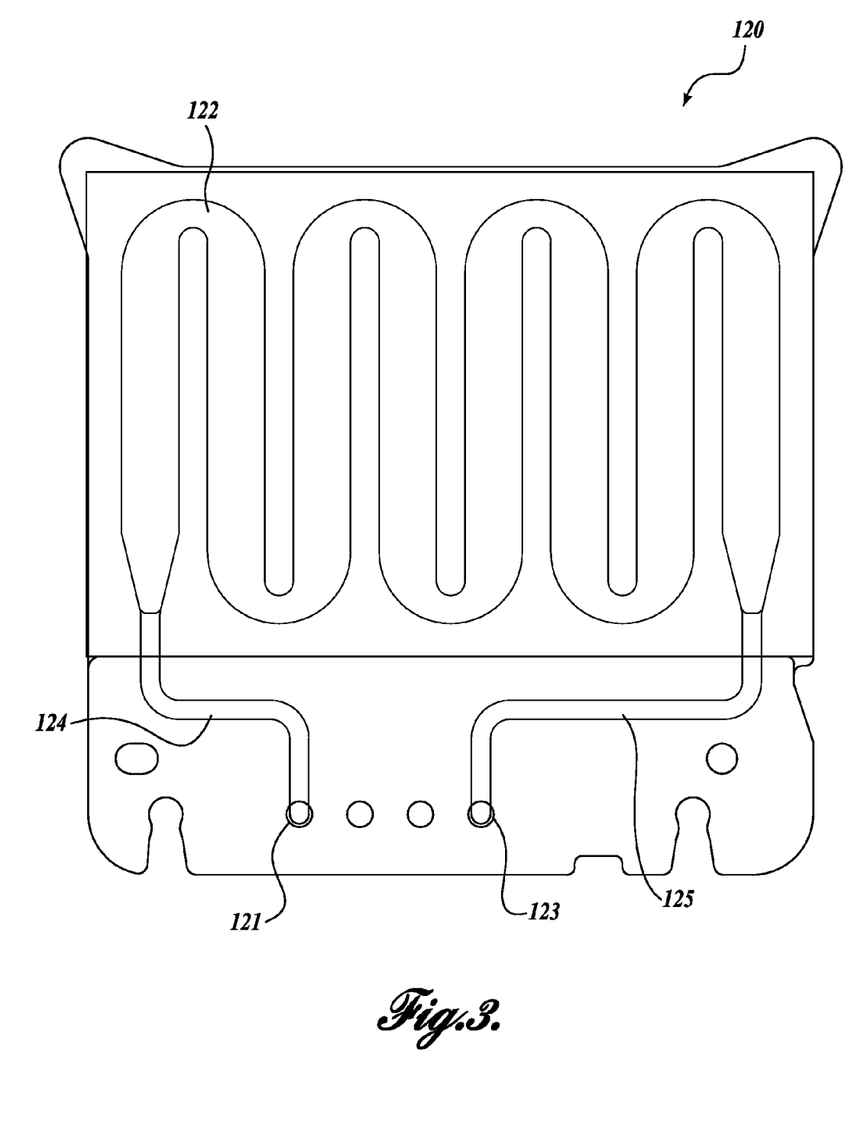
FIG. 3 is a plan view of the extraction device for the system shown in FIG. 1A.

A plan view of a representative extraction device 120 is shown in FIG. 3. The illustrated extraction device 120 defines an elongate binding channel 122 having an inner surface configured to capture nucleic acid from a suitable nucleic acid-containing sample, as discussed herein. For example, in a current embodiment the inner surface comprises an unmodified smooth glass surface, as defined above. The elongate channel 122 is serpentine with a rectangular cross-section, although other channel configurations are also contemplated. The elongate channel 122 is in fluid communication with at least one inlet port 121 and at least one outlet port 123. In the illustrated embodiment, fluid communication is provided by inlet channel 124 and outlet channel 125. The illustrated extraction device 120 is conveniently constructed by lamination of a plurality of polymer and glass layers joined by adhesives. Appropriate layers are cut or drilled to provide elongate binding channel 122, ports 121 and 123, and channels 124 and 125. In the alternative, a suitable extraction device 120 can be constructed from a die-cut block and glass slides or plates by clamping as disclosed by Reed et al., U.S. Pat. No. 8,163,535. The number of layers can be reduced through the use of molded elements. Smooth glass binding surfaces are conveniently provided by glass microscope slides, which are commonly available in approximate dimensions of 1"×3" and 2"×3".

Design parameters of extraction device 120 can be varied to optimize device performance, including nucleic acid extraction efficiency and quality, and to accommodate alternative construction methods and materials. In addition, the extraction device 120 is designed to enable a bolus of liquid to move through the elongate binding channel in a controlled manner and to spread across the inner surfaces of the binding channel without an air bubble penetrating the leading edge and becoming entrained in the bolus. Parameters to be considered in optimizing performance include: (1) the ratio of total volume to exposed glass surface area; (2) the ratio of non-glass surface area to glass surface area; (3) the ratio of straight to curved regions in the elongate binding channel; (4) the number of curves in the elongate binding channel; and (5) the width of the elongate binding channel. It is preferred that a serpentine elongate binding channel have a straight-to-curved ratio in the range of 1.0-5.0, preferably in the range or 1.0-4.0, more preferably in the range of 1.2-3.0. A straight-to-curved ratio within the range of 1.4 to 2.8 (including exemplary ratios of 1.42 and 2.62) has been found to provide superior performance. In general, a binding channel width from 2 to 8 mm has been found to be advantageous in devices of laminated and glued construction, while somewhat narrower channels (including channels having a characteristic dimension of 1 mm) can be utilized with injection molded or extruded construction, which produces smoother sidewalls. Elongate binding channel widths within the range of 5 to 7 mm are conveniently utilized. Elongate binding channel thicknesses in the range of 0.2 to 1.6 mm are generally preferred, with thicknesses of approximately 0.6 mm to 0.7 mm particularly preferred. Elongate binding channels will commonly be somewhat thinner in laminated devices than in non-laminated devices, typically not more than 1-mm thick. The ratio of width to thickness of the elongate binding channel can range from approximately 0.6 to 10 or more. Higher ratios (proportionally thinner channels) are generally preferred. Working within these parameters, exemplary extraction devices having binding channel volumes in the range of 0.5 mL to 1.5 mL can be readily constructed. Inlet channel 124 and outlet channel 125 are commonly smaller in cross-section than elongate binding channel 122. While not wishing to be bound by theory, it is believed that this smaller cross section may help to control fluid flow. It has been found that restricting the cross-sectional area of inlet channel 124 and outlet channel 125 to from 5% to 25%, more commonly from 10% to 20%, of the cross-sectional area of elongate binding channel 122 results in favorable performance. In an extraction device 120 having elongate binding channel 122 dimensions as disclosed above, inlet channel 124 and outlet channel 125 will commonly have a width of from 0.5 mm to 3 mm, more commonly 1 mm to 2 mm, and a thickness of 0.008 inch to 0.016 inch (approximately 0.2 mm to 0.4 mm).

In the embodiment shown in FIG. 2, the extraction device 120 includes or engages an adaptor 130 that is attached to the extraction device 120, and provides one or more inlet port receivers 131 and one or more outlet port receivers 133. Of course, the adaptor may alternatively be formed integrally with the extraction device. For example, the receivers 131, 133 may be female Luer-type fittings. The adaptor 130 includes tabs or panels (not shown) that cooperatively define a narrow slot that is sized to slidably receive the extraction device 120. Seals, such as gaskets or O-rings (not shown) may be used to provide a seal between the adaptor 130 and the extraction device 120.

Figure 4A:
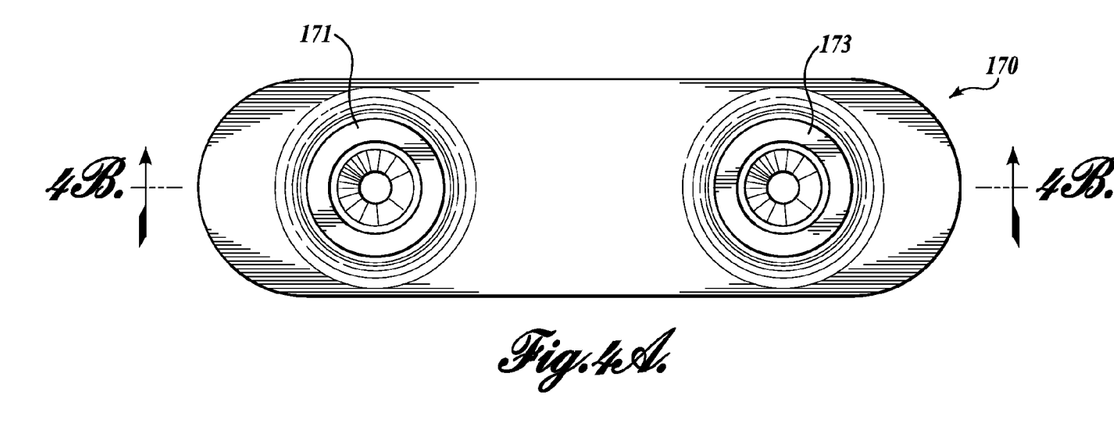
FIG. 4A is a plan view of an adaptor element that may be used within the system of the invention.
Figure 4B:
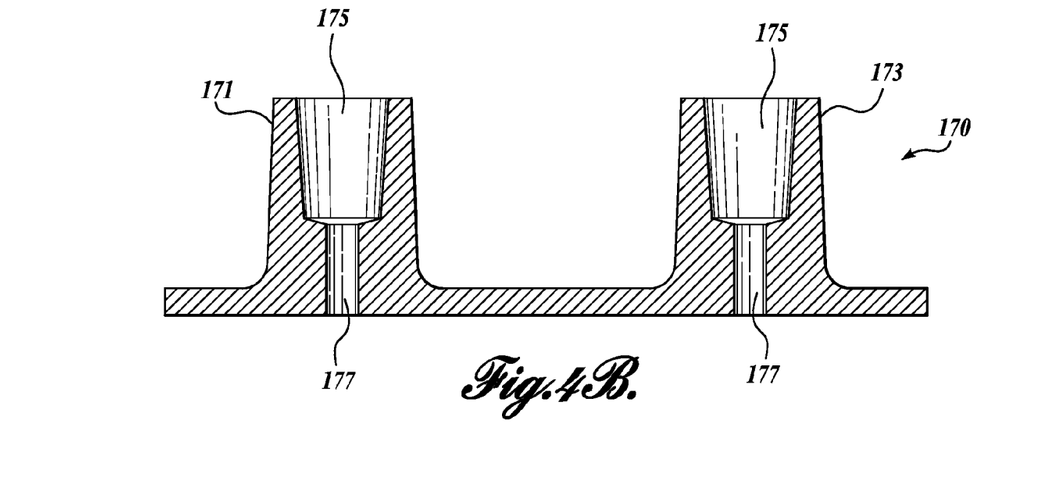
FIG. 4B is a sectional view of the adaptor element shown in FIG. 4A.

In an alternative embodiment the extraction device 120 is fitted with a unitary adaptor 170 shown in FIGS. 4A and 4B, which provides an inlet port receiver 171 and an outlet port receiver 173. Each receiver comprises a female Luer-type fitting 175 in fluid communication with a connecting lumen 177. The connecting lumen 177 is configured to engage inlet port 121 and outlet port 123. Adaptor 170 may be joined to device 120 using a conventional adhesive, such as silicone transfer tape (not shown), for example.

The extraction device 120 may preferably be constructed such that at least portions of the elongate channel 122 are transparent to permit the transmission of light therethrough. Transparent channels 122 permit the user to monitor the progress of the extraction process, and may allow for optical interrogation of captured nucleic acids.

Each extraction subsystem 110 also includes a reservoir container 140, for example a conventional syringe barrel 141, having a nozzle portion 142. The reservoir container 140 is configured to fluidly engage the inlet port receiver 131, such that the reservoir container 140 is fluidly connected to the inlet port 121. The nozzle portion 142 in the current embodiment fluidly connects to the inlet port receiver 131 through a tubular tip extender 134. For example, in certain embodiments the tip extender 134 is sized to introduce an air "bubble" into the channel 122 substantially in front of the liquid (e.g., the wash buffer) that is provided to the extraction device 120 from the reservoir container 140.

Each extraction subsystem 110 also includes a siphon tube 150. The siphon tube 150 is configured to be fluidly connected to the outlet port 123, for example through the outlet port receiver 133. A Luer-type fitting (either locking or non-locking) may also be provided. The siphon tube 150 is thereby configured to receive fluid exiting from the extraction device 120. Preferably, the siphon tube 150 is flexible, such that the position of the distal end 152 of the siphon tube 150 can be selectively adjusted by the user. The flexible siphon tube 150 permits the user to control the rate of fluid flow by adjusting the relative heights of the siphon tube 150 ends. In this way siphon tube 150 functions as a simple valve. Within an exemplary system of the present invention, a flow rate of approximately 1 mL/minute has been found to be advantageous.

Each extraction subsystem 110 also includes a receptacle 160. In a current embodiment, the receptacle 160 comprises a generally cylindrical container 161 closed at the bottom, and a vented cap 162. The vented cap 162 is configured to receive the distal end 152 of the siphon tube 150. Although it is currently preferred to provide separate receptacles 160 for each extraction subsystem 110, it is contemplated that fewer shared receptacles may alternatively be provided. For example, a single bin or rectilinear receptacle may be provided that has a single cap with multiple apertures that are sized and spaced to receive the distal end 152 of the siphon tubes 150 from a plurality, or all, of the subsystems 110. In the embodiment of FIGS. 1A-1C, the receptacle 160 is releasably attached to the bench 102 with clamps 108, to fix the position of the receptacle 160 relative to the rest of the subsystem 110. The vented cap 162 includes an aperture that slidably and frictionally receives the siphon tube 150 such that the position of the distal end 152 of the siphon tube 150 can be accurately positioned by the user. A second aperture 164 provides venting to facilitate flow into the receptacle.

To use the extraction system 100, the user provides a nucleic acid-containing fluid, for example a cell lysate solution, into one or more of the extraction devices 120. For example, a biological sample may be combined with a protease to cause proteolysis, breaking down the cell structure to release nucleic acids. Suitable proteases include, for example, proteinase K, pronase, or subtilisin. Mechanical disruption and chaotropic salt solutions may also be employed for cell lysis. The sample may then be combined with a binding buffer, as is known in the art, and with ethanol to produce a biological fluid for use with the present invention. Binding of nucleic acid to glass surfaces is commonly carried out in the presence of a buffered solution of a chaotropic salt, such as guanidinium thiocyanate, guanidine hydrochloride, sodium iodide, or sodium perchlorate; or a neutral salt such as potassium chloride or sodium acetate. Binding buffers commonly also comprise a detergent and alcohol (typically ethanol). Suitable binding buffers are known in the art. The extraction device 120 may be filled with the biological fluid prior to setting up the extraction subsystem 110, or the subsystem 110 may be used to provide the biological fluid to the channel 122. For example, in one embodiment the inlet port 121 or inlet port receiver 131 is configured to sealingly receive a pipette tip, to facilitate injection of the sample fluid into the channel 122.

In an exemplary embodiment the extraction subsystems 110 are assembled. An adaptor 130 is fastened to the extraction device 120, and the receptacles 160 are attached to the bench clamps 108. A siphon tube 150 is attached to the outlet port receiver 133 on the adaptor 130, such that the siphon tube 150 is fluidly connected with the channel 122 through the outlet port 123. The extraction device 120 is placed on the bench 102, and the distal end 152 of the siphon tube 150 is inserted through the appropriate aperture in the vented cap 162 of the receptacle 160. Preferably, the distal end 152 of the siphon 150 is initially positioned to be approximately level with or slightly below the extraction device 120.

The tip extender 134 is inserted into the inlet port receiver 131. If the biological fluid has not previously been injected into the channel 122, then a reservoir container 140 with biological fluid is fluidly connected to the tip extender 134. For example, the biological fluid may be provided in a syringe having a male Luer-type tip. The biological fluid will then gravitationally enter the channel 122. Alternatively, a plunger (not shown) may be used to inject the biological fluid into the extraction device 120. Preferably, the reservoir of biological fluid has a sufficient quantity to approximately fill the channel 122. If desired, the user may then wait for a period of time to allow the nucleic acids to adhere to the channel walls.

A reservoir of first wash buffer is then provided to the extraction device 120. For example, the assembled reservoir container 140 may be filled with a predetermined quantity of first wash buffer, a new reservoir container 140 may be attached to the tip extender 134 and filled with a predetermined quantity of first wash buffer, or a prefilled reservoir container 140 containing a predetermined quantity of first wash buffer may be attached to the tip extender 134. The first wash buffer then flows into the extraction device 120, displacing the biological fluid. Selection of wash buffers is within the level of ordinary skill in the art and will depend in part on the composition of the sample loading solution. In general, salt concentration will be reduced during the washing process, and pH will be increased slightly. If the lysis buffer contains a chaotropic salt, the initial wash will commonly also contain that salt at the same or somewhat lower concentration (e.g., 1-3 M GuSCN).

It will now be appreciated that in this embodiment the tip extender 134 defines a channel that is substantially filled with air prior to providing the first wash buffer. Therefore, the air in the tip extender 134 will be displaced into the channel 122 in front of the first wash buffer. The air bubble is believed to facilitate and improve the effectiveness of removing the fluid from the channel 122. For example, the air bubble may provide a barrier to reduce the tendency of the first wash buffer to mix with the fluid being displaced by the wash buffer. The tip extender 134 also results in the reservoir container 140 being disposed at a higher elevation with respect to the extraction device 120, so it has a higher potential energy, thereby facilitating the flow of the first wash buffer through the channel 122.

To initiate the liquid flow through the siphon tube 150, the fluid level in the reservoir container 140 must be at an elevation above the highest portion or apex of the channel defined by the siphon tube 150 when the liquid flow reaches the apex. However, if the distal end 152 of the siphon tube 150 is below the level of the extraction device 120, the flow will continue until the fluid is drained from the extraction device 120. Siphon flow is well-known. For example, using Bernoulli's equation for an inviscid, incompressible fluid, it can be shown that the velocity of the flow through a siphon depends on the height difference between the surface of the upper fluid reservoir and the drain point for the siphon. In particular, a user can control or adjust the flow rate through a siphon tube 150 by simply adjusting the vertical position of the distal end 152 of the siphon tube 150. Of course, the user can stop the flow through the siphon 150 by raising the distal end 152 above the level of the fluid in the extraction device 120. It is also contemplated that the siphon flow may stop if the air bubble enters the siphon tube 150 when the fluid level in the reservoir container 140 is below the highest elevation of the siphon tube 150, whereby the wash solution will remain in the extraction channel 122. Alternatively, if the volume of wash buffer initially provided in the reservoir container 140 is sufficient to fill the binding channel before the fluid in the reservoir of first wash buffer drops below a highest level in the siphon, flow will continue and substantially drain the wash fluid from the extraction channel 122.

Therefore, in the subsystems 110 described above, the user may position the distal end 152 of the siphon tube 150 approximately at the same level as the extraction device 120 (or a little lower, to account for viscous effects) such that the flow of the liquid, for example the first wash buffer, will stop when the reservoir container 140 and the tip extender 134 are empty. The first wash buffer will therefore remain in the extraction device 120 until further action is taken. Alternatively, the user may position the distal end 152 sufficiently lower than the extraction device 120 such that the first wash buffer will continue to flow out of the extraction device 120 and into the receptacle 160. It will also be appreciated that the user can control or adjust the rate of flow through the extraction device 120 by adjusting the position of the distal end of the siphon tube 150.

After the flow of the first wash buffer stops, e.g., either the first wash buffer substantially fills the extraction channel 122, or the first wash buffer has been substantially disposed in the receptacle 160, a second wash buffer may be used to further remove non-nucleic acid material from the channel 122, and or to better prepare the channel 122 for additional processing, for example, for drying. The second wash buffer may be provided, for example, by refilling the existing reservoir containers 140 with the second wash buffer or by providing a pre-filled reservoir container 140 to replace each existing reservoir container. In the alternative, a pre-filled reservoir container 140 may comprise a plurality of individually sealed chambers, each containing a reagent solution (e.g., wash buffer). Each solution is released in turn by puncturing its respective seal. Pre-filled reservoir container 140 may further comprise an integral syringe as disclosed above.

If the distal end 152 of the siphon tube 150 was positioned such that the first wash buffer remains in the channel 122, it will be appreciated that the tip extender 134 will ensure that an air bubble is introduced between the first and second wash buffers. The second wash buffer is similarly allowed to flow through the channel impelled by gravity and by flow through the siphon tube 150. It will be appreciated that the user may change the position of the siphon tube 150 between the first and second buffer washes, for example, to change the flow rates and/or to control whether the flow will stop before the wash buffer has substantially exited the channel 122. Alternatively, it is contemplated that the siphon tubes 150 may be provided with a valve (not shown) to control the flow. For example, if the siphon comprises a pliable tube, an adjustable clamp may be provided on the tube to control the flow rate. Alternatively, a flow restrictor may be positionable over the distal end of the siphon tube 150. An attachable flow restrictor may be particularly suitable if the siphon tubes 150 are formed from a rigid or semi-rigid material.

It is contemplated that additional buffer solutions may also be used, in the same manner as described above, until a desired condition within the extraction channel 122 is achieved. For example, additional wash buffers having varying compositions may be used.

After all desired buffers have been applied through the extraction channels 122, the user may optionally dry the channels 122, for example, to ensure that all of the ethanol or other undesirable liquids have been removed. In a particular embodiment, the extraction channels 122 are connected to an air blower pump (not shown) through the inlet ports 121, and air is blown through the channels 122 for a predetermined period of time. In an alternative embodiment, a container of pressurized gas, for example, a conventional $CO_2$ cartridge, is attached to the inlet ports 121 (for example, through a throttle or regulator) and the gas is directed through the channel 122 to dry the channel.

The extraction device 120 retains a significant portion of nucleic acids that were in the biological sample. The extraction devices 120 may therefore be interrogated directly, for example using optical or chemical means, or may be packaged and transported to a suitable laboratory for further processing. It has been found that nucleic acids bound to unmodified smooth glass surfaces and dried are stable for extended periods, typically up to a week for RNA and several months for DNA. Alternatively, a suitable elution solution may be provided to the extraction channel 122 to extract the captured nucleic acids from the extraction channel 122. For example, after drying the channel 122, a new receptacle 160 may be provided, and a reservoir container 140 containing the elution solution may be provided to the inlet port 121 and the eluate captured in the new receptacle 160.

It will also be appreciated that an extraction system similar to that disclosed above may readily be provided in a kit form, for example, to permit isolation of nucleic acid outside of a conventional laboratory. For example, a kit may include some or all of: (1) a swab, for example a nasal swab; (2) a stabilizing buffer, such as a universal transport medium, containerized to receive the swab; (3) a sample preparation syringe; (4) a lysing agent, for example, a protease; (5) a quantity of ethanol; (6) a quantity of binding buffer; (7) an extraction device, for example, the extraction device 120, adaptor 130, and tip extender 134 described above; (8) one or more reservoirs of washing buffer; (9) a waste receptacle; (10) a siphon; (11) a support apparatus; and/or (12) a pressurized gas source, such as an air pump or gas cartridge. In an exemplary embodiment, the lysing agent is a protease that is dried and disposed in the sample syringe. In another embodiment, a plurality of the above-disclosed reagents are packaged in a multi-chambered container and separated by one or more frangible seals. For example, a two-compartment package containing a chaotropic salt solution and ethanol in separate compartments may be provided. After the biological sample is added to the chaotropic salt solution, the package is twisted or compressed to break the frangible seal and allow the ethanol to combine with the sample.

To use the exemplary kit disclosed above, a biological specimen is obtained with a swab and stabilized with universal transport medium. Viral transporting kits are available from commercial suppliers (e.g., Becton Dickinson and Co., Franklin Lakes, N.J.). The stabilized specimen is drawn into the syringe containing the lysing agent and, optionally, a mixing ball, and is mixed to produce the desired biological lysate. The binding agent (with or without ethanol) is then drawn into the syringe and allowed to mix, to produce the biological sample containing nucleic acids. The extraction device 120 is placed on a suitable support, and the siphon tube 150 and receptacle 160 are assembled and positioned with respect to the extraction device 120. After a suitable time, the syringe is connected to the inlet port receiver 131 of the adaptor 130, and the binding channel 122 is filled with the biological sample. After a suitable binding time (typically 5 to 30 minutes), a reservoir of washing buffers is connected to the inlet port receiver 131, and flows through the extraction device 120 to remove the biological sample, while nucleic acids remain captured by the extraction channel 122. If desired, additional washing buffers may be used.

Figure 5:
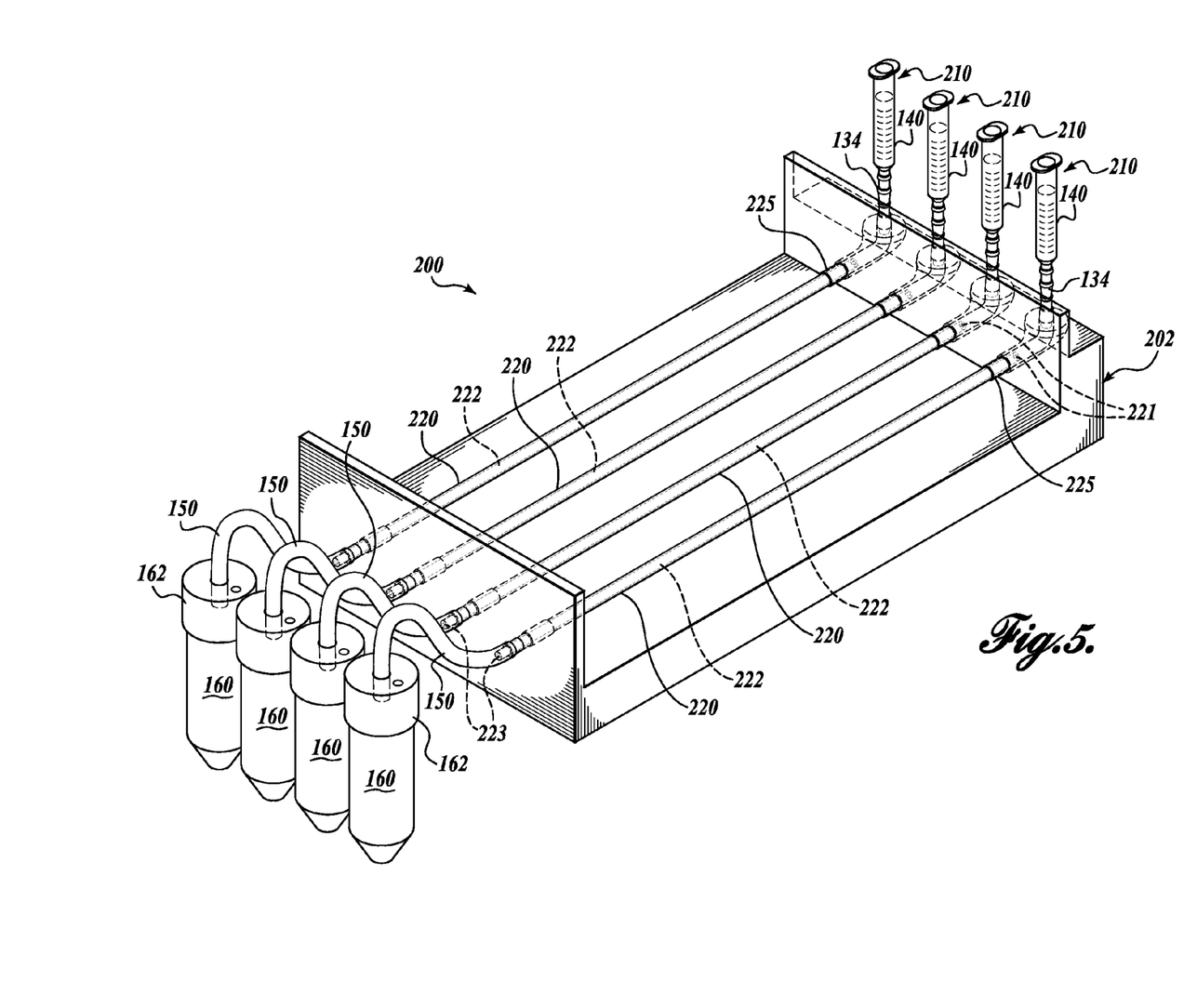
FIG. 5 illustrates another embodiment of a system for extracting nucleic acid from a sample in accordance with the present invention, using tubular extraction devices.

Another embodiment of a nucleic acid extraction system 200 in accordance with the present invention is shown in FIG. 5. In this embodiment, a bench 202 supports a plurality of tubular extraction subsystems 210. Those skilled in the art will recognize that other supports may be employed or the support may be omitted altogether, as disclosed above. Although four extraction subsystems 210 are shown, a particular system may use more or fewer subsystems 210. The subsystems 210 each include a reservoir container 140 that is removably attached to an inlet port 221 of an elongate tubular extraction device 220 through a tip extender 134. The extraction device 220 in this embodiment defines an extraction channel or lumen 222 that is configured to capture nucleic acid from a biological specimen containing nucleic acid. The distal end of each device 220 includes an outlet port 223 that connects to a vented receptacle 160 through a siphon tube 150.

In the exemplary embodiment of FIG. 5, the proximal end of each device 220 is attached to the bench 202 with a retention element 225, for example a polyurethane tube that is sized to sealingly engage the proximal end of the device 220, and fluidly connects the extraction lumen 222 with the tip extender 134 and reservoir container 140.

The distal end of each device 220 is sized to sealingly engage a siphon tube 150.

The extraction system 200 operates in a manner very similar to the extraction system 100 described above. The extraction lumens 222 are filled with a sample containing nucleic acid, for example a lysate in a binding buffer. The sample may be introduced gravitationally into the extraction lumens 222, for example by inserting a syringe containing the sample into the tip extender 134. Optionally, the syringe may be used to force the sample containing nucleic acid into the lumen 222. After the nucleic acids have had time to bind to the smooth inner surface of the devices 220, a wash buffer may be introduced into the extraction lumen 222, displacing the sample, which is thereby forced through the siphon tube 150 and into the receptacle 160. As discussed above, a beneficial air bubble may thereby be introduced between the wash buffer and the sample from tip extender 134. The distal end of the siphon 150 may be adjusted to control the flow rate through the lumen 222 and/or to control whether the wash buffer empties from the lumen 222 prior to the introduction of another wash buffer. After all desired buffers have been applied, the lumens 222 may be dried by the application of a compressed gas through the lumen 222.

Although the embodiment of FIG. 5 illustrates the devices 220 as essentially straight, uniform tubes, it will be appreciated that the system 200 may be made more compact, and/or the length of the lumens 222 may be increased, by forming the devices as tubes that are not straight, for example serpentine or spiral tubes. Such serpentine or spiral tubes may be enclosed in protective covers or boxes for protection and ease of handling, for example. It is also contemplated that the tubes may be constructed in multiple segments that are joined to define an elongate lumen 222. For example, connectors joining the segments may be provided with restrictors that operate to slow the flow through the lumen. In particular, a variety of connector designs and/or a variety of tube designs may be desirable to accommodate particular applications. For example, it may be desirable to provide tubes with larger-diameter lumens and/or without flow restrictors for applications with higher viscosity fluids.

When employing devices 220 for the extraction of nucleic acids from low-viscosity fluids it will frequently be desirable to slow fluid flow by providing one or more restrictors, which are conveniently positioned within, or are integral with, inlet port 221 and/or outlet port 223. Such restrictors will typically have an inner diameter of 2.7 mm-0.25 mm.

Although the current embodiments use tip extenders to establish the reservoir heights and to introduce bubbles into the flow, it will be apparent to persons of skill in the art that other means may provide similar functionality. For example, the extraction devices may be designed with integral upright channels at the inlet ports, and/or the reservoirs may be suitably designed to provide the desired reservoir height.

It will also be appreciated, and it is contemplated by the present invention, that the effective surface area of the extraction devices 220 may be increased, for example, by constructing the devices with a plurality of generally concentric tubes and/or a center rod.

In the current system 200 individual reservoir containers are provided for each extraction subsystem 210, and separate receptacles are similarly provided. It will be appreciated, however, and is contemplated by the present invention, that a single plenum may be used to provide a reservoir to a plurality of extraction devices 220, and/or a single receptacle may be used to receive fluids from a plurality of extraction devices.

EXAMPLE 50-100 µL, of whole blood is pipetted into a 1.7-mL tube and diluted to 500 µL with sterile water. Forty µL of 5 mg/mL Proteinase K is added, and the solution is mixed well and incubated at 37° C. for at least 20 minutes. 500 µL lysis reagent (28.7 g guanidine hydrochloride, 25 ml 0.1 M sodium citrate pH 6.5, 2.5 mL 0.2 M EDTA, 1 mL TRITON X-100, 3 mL TWEEN-20) is added. The solution is then cooled, and 500 µL ethanol is added. The contents of the tube are mixed, and the contents are drawn into a syringe having a male Luer-type tip. The prepared sample is then injected into channel 122 of extraction device 120 using the syringe plunger (not shown).

Extraction subsystem 110 is assembled as shown in FIGS. 1A-2 using an empty 3-mL syringe barrel as reservoir container 140. The injected sample is allowed to stand in the channel 122 for about thirty minutes.

The reservoir container 140 is filed with 3 mL of the first wash buffer, and the buffer is allowed to slowly flow through channel 122 and into receptacle 160 over approximately three minutes. After the first wash buffer has drained from the reservoir container 140 and an air bubble has formed at the trailing edge of the buffer, the reservoir container 140 is filled with 3 mL of a second wash buffer. The second buffer is then allowed to flow through channel 122 and into receptacle 160 over approximately three minutes. The reservoir container 140 is then filled with another 3 mL portion of the second wash buffer. The second buffer is then allowed to flow through the channel 122 and into the receptacle 160 over approximately 3 minutes. The extraction device 120 is then connected to an air pump and the binding channel 122 is air-dried for 4 minutes at a flow rate of about 3 cubic feet per hour. The extracted nucleic acid is then eluted from the channel with 100-200 µL of water. For example, the user may elute the bound nucleic acid from the inner surface with a buffer that exhibits a change in fluorescence intensity in the presence of nucleic acid.

While illustrative embodiments have been illustrated and described, it will be appreciated that various changes can be made therein without departing from the spirit and scope of the invention.

The embodiments of the invention in which an exclusive property or privilege is claimed are defined as follows:

1. A process for extracting nucleic acid from a solution, the process comprising:
   providing a conduit comprising a binding channel having an inner surface, a first port, and a second port, wherein the first port and the second port are in fluid communication with the binding channel;
   introducing the solution containing nucleic acid into the binding channel such that the solution is in contact with the inner surface and at least a portion of the nucleic acid binds to the inner surface to produce a bound nucleic acid and a residual solution;
   positioning a siphon tube having a first end connected to the second port such that a second end of the siphon tube is open to ambient pressure, a portion of the siphon tube is disposed at an elevation above the binding channel and the second end is configured to be adjusted vertically to control a fluid flow and wash; and
   fluidly connecting a reservoir of first wash buffer disposed at an elevation above the binding channel to the first port such that gravity forces the first wash buffer to flow through the first port into the binding channel, the first wash buffer thereby displacing the residual solution from the binding channel and through the siphon tube, whereby the bound nucleic acid is washed.

2. The process of claim 1, further comprising introducing a gas bubble into the binding channel between the solution containing nucleic acid and the first wash buffer.

3. The process of claim 2, wherein the gas bubble is air.

4. The process of claim 3, wherein the reservoir of first wash buffer is connected to the first port through an elongate tube that is initially filled with air, and wherein the gas bubble is introduced into the binding channel by the first wash buffer displacing the air from the elongate tube into the binding channel.

5. The process of claim 1, further comprising:
   waiting for the reservoir of first wash buffer to flow into the binding channel, and then fluidly connecting a reservoir of second wash buffer disposed at an elevation above the binding channel to the first port such that gravity forces the second wash buffer to flow through the binding channel displacing the first wash buffer whereby the first wash buffer flows through the siphon tube.

6. The process of claim 1, wherein the second end of the siphon tube is disposed within a vented outflow receptacle.

7. The process of claim 1, wherein the second end of the siphon tube is disposed at an elevation lower than the first end of the siphon tube.

8. The process of claim 1, further comprising controlling a flow rate of the first wash buffer through the binding channel by setting the elevation of the second end of the siphon tube.

9. The process of claim 1, wherein the binding channel comprises a lumen formed by a smooth glass tube.

10. The process of claim 1, wherein the binding channel comprises a flow path cooperatively defined by a plurality of stacked, planar lamina.

11. The process of claim 1, wherein the binding channel is serpentine.

12. The process of claim 1, wherein the conduit further comprises: an inlet channel providing a fluid connection between the first port and the binding channel; and an outlet channel providing a fluid connection between the second port and the binding channel.

13. The process of claim 1, further comprising removing the first wash buffer from the binding channel by flowing gas from a source of pressurized gas through the binding channel.

14. The process of claim 1, further comprising drying the bound and washed nucleic acid by flowing gas from a source of pressurized gas through the binding channel.

15. The process of claim 1, wherein the solution containing nucleic acid comprises a lysate solution including ethanol.

16. The process of claim 1, further comprising eluting the bound nucleic acid from the inner surface.

17. The process of claim 16, wherein the bound nucleic acid is eluted with a buffer that exhibits a change in fluorescence intensity in the presence of nucleic acid.

18. The process of claim 1, wherein the inner surface of the binding channel is essentially free of nucleic acid-specific binding sites.

19. The process of claim 1, wherein the inner surface of the binding channel comprises nucleic acid-specific binding sites.

20. The process of claim 1, wherein the inner surface of the binding channel comprises a glass surface.

21. The process of claim 1, wherein the inner surface of the binding channel comprises an unmodified, smooth glass surface.

22. The process of claim 1, wherein the binding channel has at least one dimension that is less than 1.0 mm.

23. The process of claim 1, wherein the reservoir of first wash buffer has a reservoir volume that is sufficient to fill the binding channel before the fluid in the reservoir of first wash buffer drops below a highest level in the siphon.

24. A kit for extracting nucleic acid from a sample comprising: a device defining an elongate binding channel having an inner surface that is suitable for capturing nucleic acids in a solution, the device further comprising a first port fluidly connected to the elongate binding channel, and a second port fluidly connected to the elongate binding channel; a reservoir comprising a barrel with a body portion defining a first volume and a tip portion defining a through lumen fluidly connected to the first volume, wherein the tip portion is configured to fluidly engage the first port; and a siphon tube configured to fluidly engage the second port and to be adjusted vertically to siphon a liquid from the elongate binding channel.

25. The kit of claim 24, wherein the reservoir contains a wash buffer solution.

26. The kit of claim 24, wherein the kit further comprises a second reservoir containing a second wash buffer solution different from the first wash buffer solution, the second reservoir having a tip portion defining a lumen and configured to fluidly engage the first port.

27. The kit of claim 24, wherein the kit further comprises a vented outflow receptacle having an aperture sized to receive the siphon.

* * * * *